United States Patent [19]

Klose et al.

[11] Patent Number: 4,557,600

[45] Date of Patent: Dec. 10, 1985

[54] PROCESS AND DEVICE FOR THE CONTROL AND MIXING OF A FLUID CURRENT SUBJECTED TO CENTRIFUGAL FORCE

[75] Inventors: Sigmar Klose, Berg; Manfred Pasch; Wolfgang Kleemann, both of Tutzing; Friedhelm Vieth, Haunshofen; Herbert Buschek, Weilheim, all of Fed. Rep. of Germany

[73] Assignee: Boehringer Mannheim GmbH, Mannheim, Fed. Rep. of Germany

[21] Appl. No.: 413,011

[22] Filed: Aug. 30, 1982

[30] Foreign Application Priority Data

Sep. 1, 1981 [DE] Fed. Rep. of Germany ....... 3134560

[51] Int. Cl.[4] .......................... G01N 1/10; G01N 21/07
[52] U.S. Cl. ..................................... 356/246; 436/45; 356/427
[58] Field of Search .......................... 356/427, 246, 72; 422/72; 494/16; 436/45

[56] References Cited

U.S. PATENT DOCUMENTS

| | | | |
|---|---|---|---|
| 3,586,484 | 6/1971 | Anderson | 356/72 X |
| 3,795,451 | 3/1974 | Mailen | 356/246 |
| 3,801,004 | 4/1974 | Martin | 356/427 |
| 3,829,223 | 8/1974 | Hamel | 356/246 |
| 3,873,217 | 3/1975 | Anderson et al. | 356/427 |
| 4,035,156 | 7/1977 | Shumate, II | 356/427 |

*Primary Examiner*—Vincent P. McGraw
*Assistant Examiner*—S. A. Turner
*Attorney, Agent, or Firm*—Felfe & Lynch

[57] ABSTRACT

A process and a device for the centrifugal control and mixing of a limited volumes of fluid, especially in the rotor of a centrifugal analyzer, has at least one baffle chamber, in a flow canal for the fluid the volume of which is greater than the volume of fluid. It is so shaped that, when the device is rotated at a sufficiently high first speed of rotation, the fluid remains in it. An outlet canal is connected to the baffle chamber the fluid. At least a part thereof lies closer to the axis of rotation than the fluid surface during the rotation with the first speed of rotation. The walls of the outlet canal consist of a material which is wettable by the fluid and, in combination therewith, have cross-section which forces the fluid out of the baffle chamber; by boundary surface force when the device is rotated at a second, slower speed.

17 Claims, 9 Drawing Figures

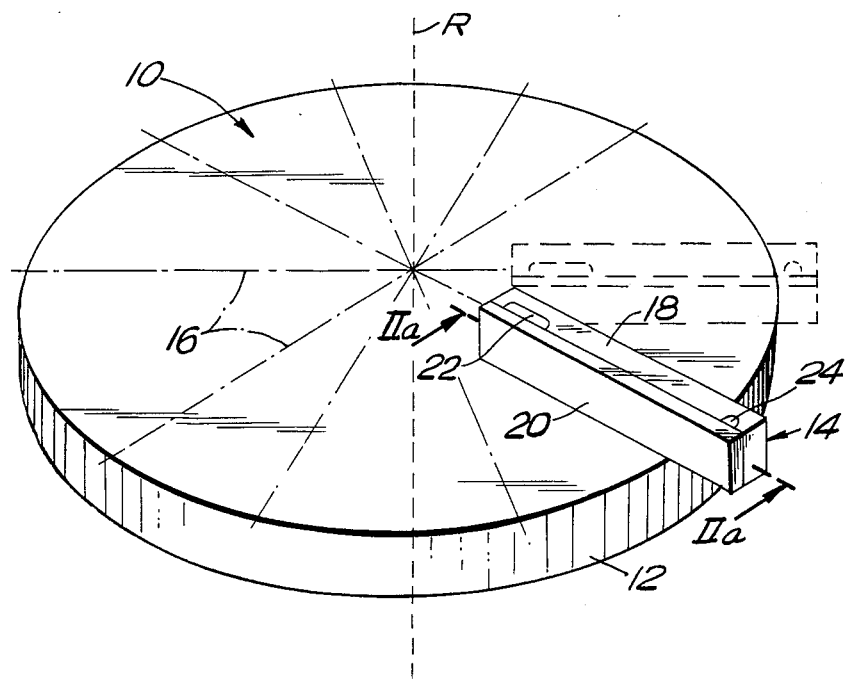
FIG. 1
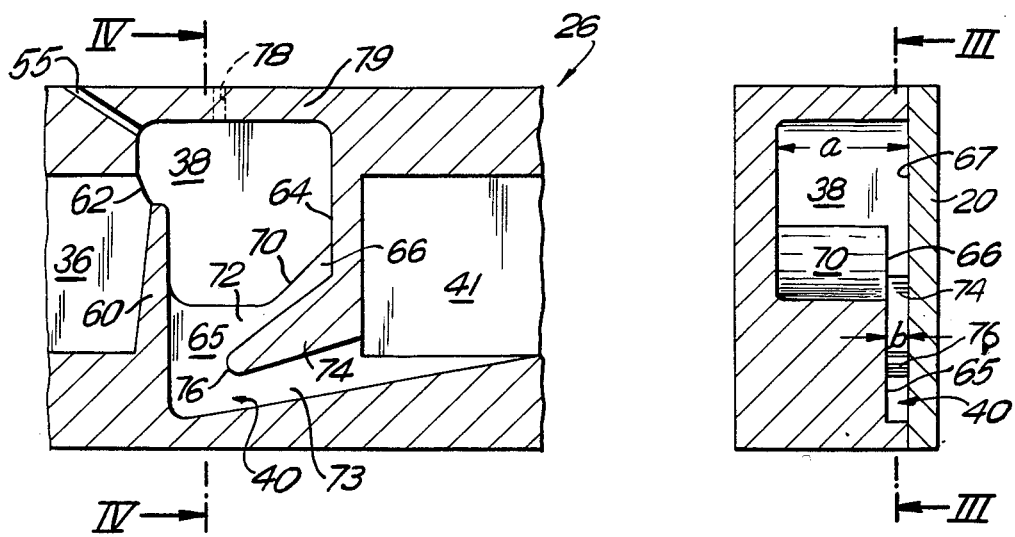
FIG. 3
FIG. 4

PROCESS AND DEVICE FOR THE CONTROL AND MIXING OF A FLUID CURRENT SUBJECTED TO CENTRIFUGAL FORCE

BACKGROUND OF THE INVENTION

The present invention relates to a method and apparatus for the control and mixing of a limited volume of fluid when subjected to centrifugal force, for example in the rotor of a centrifugal analyzer.

The present invention is especially suitable for use in centrigual analyzers such as have been conventionally used for a number of years for chemical analysis, especially in clinical chemistry. Such analyzers are especially characterized by their relatively simple mechanical construction and, consequently, great dependability. In general, they have circular, symmetrically-constructed rotors with a plurality of radial flow canals which connect several chambers. Usually, each flow canal has, from the inside towards the outside, a trough-shaped reagent chamber, a sample chamber and a measurement chamber which, in the case of the known devices, is constructed as an optical cuvette. The reagent chamber and the sample chamber are usually filled with a liquid reagent and sample to be investigated (usually blood serum or plasma) while the rotor is stationary. Thereafter, the rotor is rotated comparatively rapidly (on the order of 1000 r.p.m.) so that the reagent is forced centrifugally through the flow canal into the sample chamber and the sample and reagent flow together through the continuation of the flow canal into the optical cuvette. During the rotation of the rotor, the optical absorption of the sample and reagent reaction mixture is measured in the various cuvettes by means of appropriate detectors and an electronic circuit which synchronizes the detectors to the rotation of the rotor. A special advantage of centrifugal analyzers is that the course of the reaction in each cuvette of the rotor can be monitored practically simultaneously and an especially exact evaluation is then, in particular, possible when the kinetics of the reaction give the desired information regarding a particular component of the sample fluid. The principle of the centrifugal analyzer is known from numerous publications so that a detailed description thereof is not necessary here.

However, a disadvantage of the known centrifugal analyzers is that they only permit relatively simple courses of reaction. As described above, one or, in exceptional cases, several reagent fluids are mixed in one operating step with the sample and transported by centrifugal force into the cuvette. Therefore, the reaction must, of necessity, by a one-stage reaction which means, in particular, that there is no possibility of first allowing a pre-reaction to take place with a first reagent and then, possibly after an appropriate incubation time, of carrying out a second reaction with a further reagent. However, such two-stage reactions are of considerable importance, especially in clinical analysis. Federal Republic of Germany Patent Specification No. 20 09 993 describes, in connection with another problem, a device which permits a control, i.e. an interruption, aimed liberation and deflection, of a fluid flow in a device of the initially mentioned type. In this known device, the flow canal for the fluid is provided with hollow chambers which, in each case, are connected by a syphon-like canal with the subsequent hollow chamber. That part of the syphon which lies closest to the axis of rotation is closer to this than the fluid level in the hollow chamber during rotation of the rotor. Only the hollow chamber and the subsequent part of the syphon-like canal are thereby first filled with the fluid. The further flow of the fluid from the hollow chamber into the chamber following the syphon is brought about by applying an appropriate gas pressure to the hollow chamber, which forces the fluid through the syphon. The introduction of the necessary pressurized gas to the rotor can only take place in its center and is, of necessity, expensive to construct. It requires a special rotor design, due to which the construction of the rotor is, in other regards, subject to undesired limitations.

Federal Republic of Germany Patent Specification No. 20 22 084 describes a device in which a fluid, for example blood, is, for the purpose of centrifuging off solid components of the fluid, centrifuged in chambers from which, upon stopping the rotor, the fluid runs off due to gravity in canals leading centripetally obliquely downwardly. This device requires a considerable amount of space and, if one would think of using it for the control of the fluid flow, it involves the risk that a part of the fluid flows further in an uncontrollable manner through the relatively large canals.

Another problem of the known centrifugal analyzers is mixing up the fluid. It is very important for the analysis that the reagent and sample are mixed up in a short time and as completely as possible before they pass into the measurement cuvette. In order to achieve this, a number of improvements to centrifugal analyzers have already been suggested, for example the use of variously shaped flow impedances which are intended to improve the mixing of the fluid flowing through them. Another known device for mixing sample and reagent in a centrifugal analyzer is described in U.S. Pat. No. 3,795,451. The rotor thereof has a sample chamber which is separated by a vertical wall from the radially outward measurement cuvette. The upper end of the separating wall is provided with a passage the size of a capillary. Radially inwardly from the sample chamber, there is a reagent chamber, the separating wall between these being inclined obliquely downwardly and having on its lower end a passage with the dimensions of a capillary. In operation, the reagent is forced at a low speed of rotation into the sample chamber, which simultaneously serves as a mixing chamber. After a predetermined time, the speed of rotation is increased, the reaction solution thereby being forced out of the sample chamber into the cuvette. With such a device, mixing up of reagent and sample in the sample chamber is possibly improved, but a simultaneous control of the course of the reaction in the above-discussed sense for achieving multiple treatment of the reaction solution is not achieved and is also not an object of the described device.

SUMMARY OF THE INVENTION

It is an object of the present invention to achieve a control, i.e. a deflection, interruption and liberation, of a fluid flow of limited volume and, at the same time, a mixing up of the fluid in a device, when rotated, which operates dependably, without movable parts and only occupies a small space.

Thus, according to the present invention, there is provided a device for the control and mixing of a fluid current when rotated, for example on the rotor of a centrifugal analyzer. The amount of fluid to be controlled is limited, and the device has at least one baffle chamber, the volume of which is greater than the maximum volume of fluid. The baffle chamber is so shaped that, when the device is rotated with a sufficiently high first speed of rotation, the fluid remains in it. An outlet canal is connected to the baffle chamber, which canal is so constructed and arranged that at least a part thereof lies closer to the axis of rotation than the surface of the fluid during the rotation with the first speed of rotation. The walls of the outlet canal consist of a material wettable by have a fluid and the cross-section such that, when the device is rotated with a second speed of rotation which is smaller than the first speed of rotation, the fluid is forced by boundary surface force into the outlet canal.

The present invention also provides a process for the control and mixing of a current of fluid in such a device when subjected to centrifugal force. The fluid is driven by the centrifugal acceleration, which is greater than the gravitational acceleration, into the baffle chamber and, after the desired period of residence in the baffle chamber, the speed of rotation is reduced to such an extent that the fluid, driven by boundary surface force, fills the outlet canal connected with the baffle chamber.

In contradistinction to the previously mentioned known device, the device of the present invention is thus characterized in that the outlet canal of the baffle chamber is not connected directly radially outwardly with the next chamber but at least partly lies closer to the axis of rotation than the fluid surface which forms in the baffle chamber during the rotation with a sufficiently high first speed of rotation. According to the process of the present invention, this first speed of rotation is to be at least about so high that the centrifugal acceleration resulting therefrom in the baffle chamber corresponds approximately to the gravitational acceleration. In this case, the fluid has a downwardly and inwardly inclined meniscus but, during the rotation with the first speed of rotation, remains in the baffle chamber and possibly, similarly to the previously mentioned syphon-like construction, in a part of the outlet canal.

In contradistinction to the device described in U.S. Pat. No. 3,795,451, the further flow of the fluid is not achieved by an increase of the speed of rotation but by a reduction of the speed of rotation. In this connection, it is important that the outlet canal of the baffle chamber consists of a material which is wettable by the fluid. In this case, the forces of adhesion which act between the wall of the canal and the fluid are greater than the cohesion forces between the fluid particles and, consequently, the fluid tends to wet the wall bounding it. It is thus possible to speak of a positive boundary surface energy which results in a corresponding boundary surface force. The cross-section of the outlet canal is so constructed that this boundary surface force or capillary force sucks the fluid into the outlet canal in the absence of other forces and possibly also without support by the gravitational force.

In order to be able to include a suction action, the outlet canal must be made capillary-active.

Especially preferred is a rectangular cross-sectional construction of the outlet canal in which the smaller dimension of the rectangle is so small that a suction action is achieved to the desired extent, whereas the longer dimension of the cross-sectional rectangle is so dimensioned that, in all, there results the necessary cross-section for the desired flow.

According to the process of the present invention, the fluid, as mentioned, enters into the outlet canal upon reduction of the speed of rotation and fills this. By appropriate means, described in the following in more detail, it can be further transported from the outlet canal into a corresponding reception chamber so that the desired control of the fluid is achieved solely by a corresponding variation of the speed of rotation. Surprisingly, the narrow, capillary-shaped construction of the outlet canal does not result in a blocking action which have to be overcome by an increase of the speed of rotation, but rather the capillary force can be advantageously used, with the help of the constructional measures according to the present invention, to achieve further passage of the fluid without the support of other forces and especially of gravitational force or of a gas pressure. Simultaneously, several fluid components introduced into the baffle chamber are intensively and quickly mixed up. It is most unexpected that such a device, housed especially in a centrifugal analyzer in a small space and operating with very small cross-sectional dimensions, functions very dependably, as has been demonstrated by practical experience with the device according to the present invention.

The present invention will now be explained in more detail in the following, with reference to the embodiments illustrated in the accompanying drawings, preferred embodiments of the present invention and the advantages thereof also being discussed. Thus, in the accompanying drawings:

BRIEF DESCRIPTION OF THE DRAWINGS

FIG. 1 is a schematic illustration of the rotor of a centrifugal analyzer with an insert element present thereon which contains the flow canal for the fluid;

FIG. 3 is a detailed view of a control and mixing device according to the present invention in an insert element according to FIG. 2;

FIG. 4 is a cross-section along the line IV—IV in FIG. 3; and

DETAILED DESCRIPTION OF THE PREFERRED EMBODIMENTS

Figure 2A:
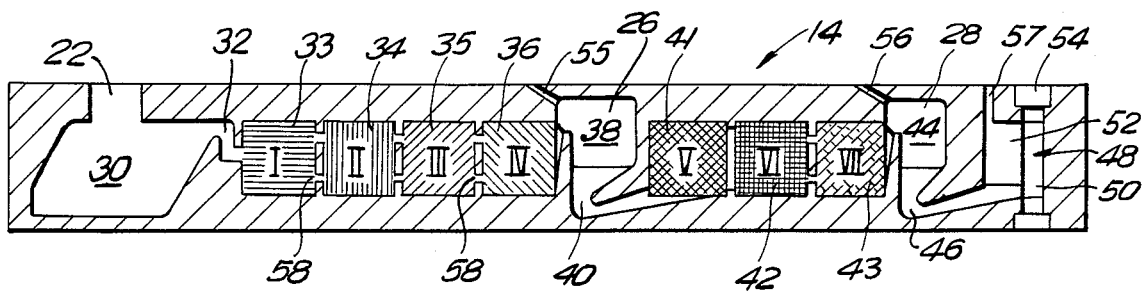
FIGS. 2a and 2b show cross-sections from the side and the top of a corresponding insert element with the device according to the present invention.

In the following, the present invention is explained on the bases of a particular rotor of a centrifugal analyzer, such as that disclosed in copending U.S. application Ser. No. 323,205, filed Nov. 20, 1981 and incorporated herein by reference, which is especially characterized in that the sample chamber and the measurement cuvette, as well as the two connection flow canals are present in an insert element separate from the base of the rotor, in which the necessary reagents are accommodated on a carrier material, for example in the form of reagent papers. However, it is to be stressed that the present invention can be used on any rotating element in which a limited volume of fluid is to be controlled and mixed in the described sense. This applies especially to rotors of centrifugal analyzers, regardless of whether they are in one piece or made up of several parts and of whether the reagents are introduced into the rotor as fluids or are present therein in solid form.

In FIG. 1, there is shown a rotor of a centrifugal analyzer, indicated in its totality by reference 10, which can rotate about an axis of rotation R. It is illustrated in a highly simplified manner and consists essentially of a rotor base 12 upon which several insert elements 14 can be fixed in different positions. However, in FIG. 1, for the sake of clarity, only one insert element 14 is illustrated and another one is indicated by broken lines. The insert elements 14 extend essentially in a radial direction along the broken lines 16. In each case, they consist essentially of a base body 18 and a cover part 20. FIG. 1 also shows a sample chamber opening 22 and a cuvette window 24.

Figure 2B:
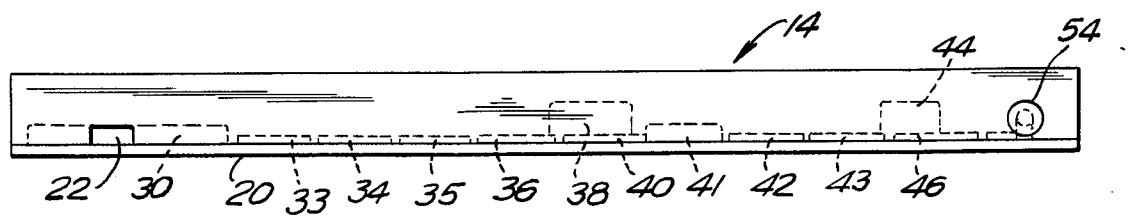

FIGS. 2a and 2b show the details of an insert element 14 which is provided with two control and mixing devices 26 and 28 according to the present invention which in the following, for the sake of simplicity, are called mixing valves. The flow canal for the fluid in the insert element comprises, from a sample chamber 30, a connecting canal 32 and four interconnected reagent zones 33 to 36 leading into a baffle chamber 38 of the first mixing valve 26. Due to the method of functioning of the mixing valve 26, which is described in detail in the following, the fluid in the flow canal passes further through the outlet canal 40 into three further reaction zones 41, 42 and 43. From there, it passes into baffle chamber 44 and, positively controlled due to the function of the mixing valve 28, into outlet canal 46 and from there into cuvette 48, which comprises an actual measurement chamber 50 and a cuvette antechamber 52. Above and below, it is provided with transparent cuvette windows 54. The two mixing valves 26 and 28, as well as the cuvette antechamber 52, are provided with ventilation canals 55, 56 and 57. The insert element 14 is assembled on the rotor so that it is arranged essentially radially with, the sample chamber closest to the center.

The reagent zones 33 to 36 and 41 to 43 are, in each case, connected with one another by overflow canals 58, can fulfill different functions and can be constructed in various ways. The zones 33 to 36 preferably contain one or more papers which are provided with dried reagents. The reagent zone 41 is, in conjunction with the function of the mixing valve 26 according to the present invention, preferably of deeper construction, which can be seen especially from the view of the insert element according to FIG. 2b. Depending upon the analysis process to be carried out, it can be desirable if this reagent field only contains an absorbent fleece as a capillary-active filling, which does not contain any reagent. In other cases, however, this fleece can also be used as a reagent carrier. The reagent zones 42 and 43 again fulfill purposes similar to the reagent zones 33 to 36 but contain reagents for a second stage of the analysis process to be carried out with the insert element 14.

In operation, a sample to be analyzed is diluted in an appropriate manner and introduced through the opening 22 into the sample chamber 30 while the rotor is stationary. Thereafter, the rotor is set in rotation so that the sample solution passes from the sample chamber into the first reagent zone 33 and through the further reagent zones 34 to 36 into the first mixing valve 26. When flowing through the reagent zones, the reagents contained therein are dissolved out and pass with the sample solution into the mixing valve 26. The manner of functioning of the reagent carriers contained in the reagent zones and the procedure of dissolving out the reagents is described in more detail in Federal Republic of German Patent Specification No. 30 44 385, corresponding to the aforementioned copending U.S. application and to which reference is here made. From the first set of reagent zones, the fluid passes, as mentioned above, into the baffle chamber 38 of the mixing valve 26 where it remains so long as a sufficiently high speed of rotation of the rotor 10 is maintained. This time is determined, in particular, by the incubation time of the reaction mixture necessary for the first process step.

The construction and function of the mixing valve 26 are described in the following in more detail, with reference to FIGS. 3 to 5.

FIG. 3 is an enlarged view of part of the cross-sectional illustration of FIG. 2a. As can be seen, the end of the reagent zone 36 adjacent to the baffle chamber is closed off by a separating wall 60 which, on the side of the reagent zone, is inclined upwardly and outwardly. Above the separating wall, there is present an inlet opening 62 into the baffle chamber 38.

In the illustrated embodiment, the baffle chamber 38 is constructed in such a manner that it is completely closed in the centrifugal direction, i.e. in FIG. 3 on the right thereof. The radially outermost part of the baffle chamber is referred to as the baffle chamber centrifugal bottom 64.

The outlet canal 40 of the baffle chamber has, as can be clearly seen from the cross-sectional view in FIG. 4, an elongated substantially rectangular cross-section. From FIGS. 3 and 4, it can also be clearly seen that the actual baffle chamber 38 is of much deeper construction (distance a), i.e. in the cross-sectional view according to FIG. 4, is very much wider than the outlet canal 40. The surface 65 bounds the outlet canal, together with the inner surface 67 of the cover 20 to a breadth b. The surface 65 extends in the region 66 into the baffle chamber 38. In the Figures, there can be seen the surface 70 which results on the radially outer side of the baffle chamber 38 from the passage from the large depth a of the baffle chamber to the small depth b of the outlet canal 70. As seen in the radial direction, i.e. in the plane of the drawing of FIG. 3, the outlet canal 40 runs, in a first section 72, radially inwardly and downwardly, i.e. with a directional component towards the axis of rotation R. In the second section 73, on the other hand, the outlet canal runs with a directional component radially away from the axis of rotation. Both sections are separated by the baffle wall 74. The part of the baffle wall 74 lying closest to the axis of rotation R is referred to as an apex 76. The second section of the outlet canal opens in a centrifugal direction into a reception chamber which, in the case of the here-illustrated mixing valve 26, is formed by the reagent zone 41. The outlet canal 46 of the mixing valve 28 opens into the cuvette antechamber 52 (FIG. 2). It is important that the end of the outlet canal, i.e. its opening into the subsequent reception chamber 41 or 52 lies further away from the axis of rotation than the radially outermost part of the baffle chamber.

Finally, in FIG. 3, there can also be seen an overflow canal 78 in the upper wall 79 of the baffle chamber 38 through which, in the case of the first speed of rotation, a volume of fluid exceeding a definite limiting value can flow away. This overflow canal 78 is only necessary when the baffle chamber 38 is to be simultaneously used in a known manner for limiting the stream volume passed further on from the mixing valve 26. In FIG. 3, it is, therefore, indicated by broken lines.

The method of function of the control and mixing device according to the present invention is described in the following in more detail, with reference to the process steps illustrated in FIGS. 5a to 5d. Above the Figures is to be found a diagram for the course of the speed of rotation of the analysis rotor, by means of which the speed of rotation programme is made clear.

Figure 5A:
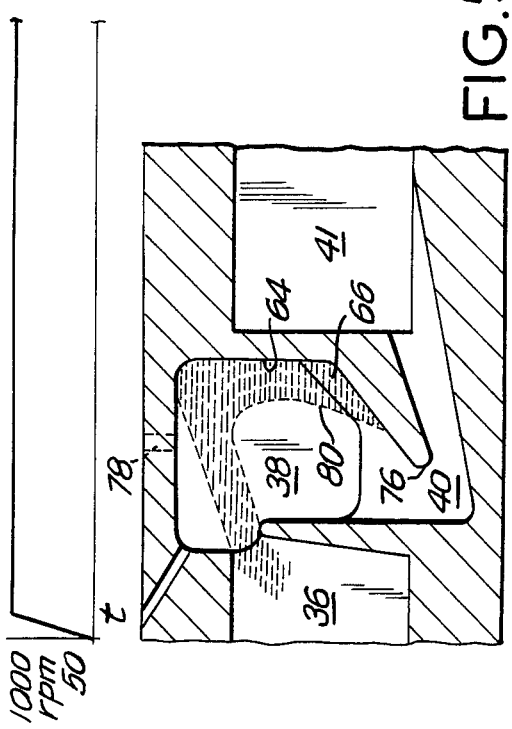
FIGS. 5a to d are illustrations corresponding to FIG. 3, from which is to be seen the course of the function of the device according to the present invention.

FIG. 5a shows the stage in which the fluid is expelled from the last reagent zone 36 of the first stage with a sufficiently high speed of rotation (for example 1000 r.p.m.) and passes into the baffle chamber 38. This speed of rotation must be so high that the fluid is forced by centrifugal force against the baffle chamber bottom 64. Depending upon the relation between the centrifugal force acting on the fluid, on the one hand, and the gravitational force, on the other hand, there is formed a more or less highly curved and tilted fluid surface 80. The speed of rotation must therefore be so great that the fluid, in the play of forces between the centrifugal force and the capillary force acting against it in the first section 72 of the outlet canal, still does not pass on further than at most up to the apex 76 in the outlet canal.

Figure 5B:
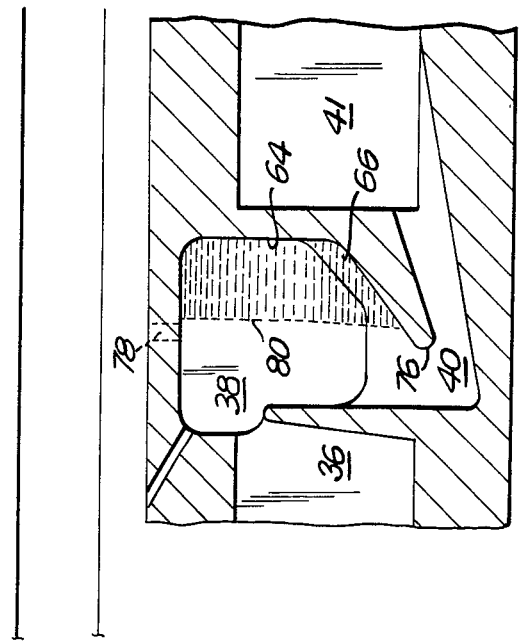

FIG. 5b shows the state during the rotation with the first speed of rotation. From this Figure, there can also be seen the function of the overflow canal 78 which is present at the place at which the fluid surface 80 ends in the case of the appropriate speed of rotation and the desired maximum volume.

Figure 5C:
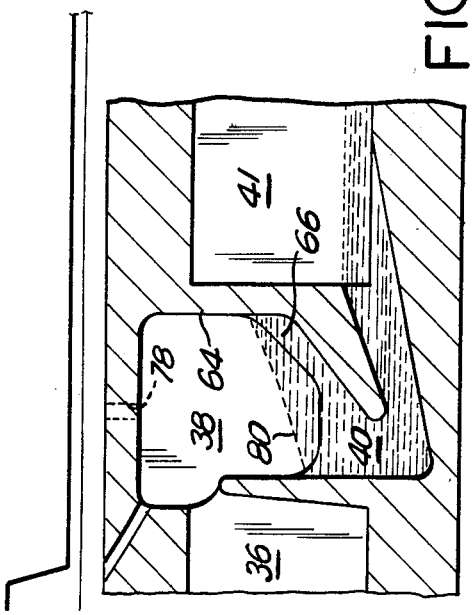

FIG. 5c shows the outflow of the fluid through the outlet canal 40. As is to be seen from the speed of rotation diagram associated with the Figure, the speed of rotation is considerably reduced, for example to about 50 r.p.m. The surface 80 thereby becomes very much less steep because the centrifugal force, in the case of this low speed of rotation, is less strong than the gravitational force. In the first section 72 of the outlet canal 40, which runs essentially counter to the centrifugal direction, the capillary force preponderates in comparison with the centrifugal force. In the second section 73 of the outlet canal, both forces act in the same direction because this has a directional component in the centrifugal direction. In this way, as can be seen from FIG. 5c, the outlet canal fills up with fluid due to the capillary force.

Figure 5D:
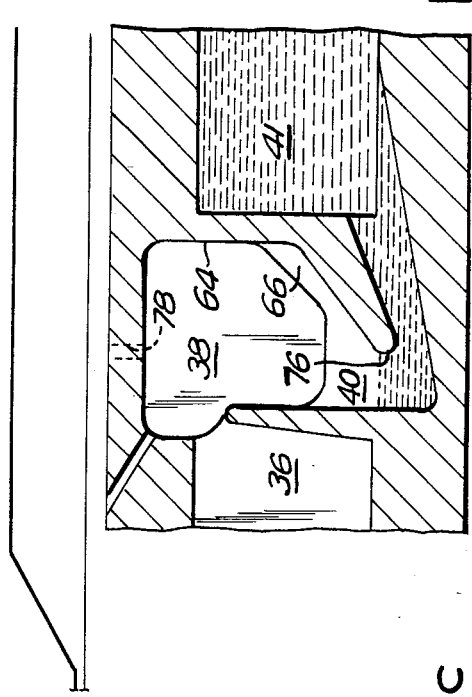

In FIG. 5d, a process stage is illustrated in which the speed of rotation is again slowly increased. This may only take place when the fluid in the outlet canal has reached a point which lies further away from the axis of rotation than the baffle chamber bottom 64. When, in this state (as shown, for example, in FIG. 5c), the speed of rotation is again slowly increased, stronger forces act on the fluid particles in the part of the outlet canal 40 facing away from the baffle chamber 38 in the centrifugal field of force than on the particles of the fluid present in the part of the outlet canal 40 on the baffle chamber side. This effect is comparable with the working principle of a gravitational suction lifter conventional in chemical laboratories. In the case of a slow acceleration of the rotor, the fluid is thereby forced into the reception chamber 41 or 52. FIG. 5d illustrates the state in which the total fluid has just passed the apex 76 and can again be accelerated to the full first speed of rotation.

The baffle chamber 38 can be constructed in various ways, the most meaningful construction for any individual case being determined experimentally. In any case, its volume capacity in the case of the first speed of rotation must be greater than the maximum volume of the fluid. In order to produce the effect according to the present invention, it is desirable when the baffle chamber 38 has a relatively small wetted surface in comparison with the volume. Since, for practical reasons, it is preferably made of the same material as the outlet canal, its surface is also wetted by the fluid. In the case of too narrow a construction of the baffle chamber 38, this effect would counter the desired capillary action of the outlet canal 40.

The outlet canal 40 itself can, in the scope of the present invention, also vary considerably. Instead of by the rectangular cross-sectional construction shown in the Figures, the desired capillary action can also be realized by an appropriate fiber filling or, for example, by a grooved profile. In any case, the force with which the fluid is drawn into the capillary gap of the outlet canal 40 is determined, on the one hand, by the wetting properties of the material and, on the other hand, by the characteristic breadth b of the capillary gap. In individual cases, the optimum relationship of capillary gap cross-section, especially of the characteristic breadth b, of the material used and of the course of the outlet canal 40 can be determined experimentally.

The construction of the outlet canal 40 illustrated in the Figures, in which this is automatically wetted in its region defined by the region 66 of the surface 65 already during the rotation with the first speed of rotation, is especially preferred since the dependability of the device according to the present invention is thereby increased.

On the other hand, however, cases of use are also conceivable in which this measure is not necessary or expedient and the outlet canal opens into the baffle chamber at a point which, in the case of rotation with the first speed of rotation is not wetted by the fluid.

The reception chamber 41 is preferably provided with a capillary-active filling or construction. This means, for example, that a fleece is present through which the fluid, when it has completely filled the outlet canal, is sucked into the reception chamber. In the case of this embodiment of the present invention, it is not necessary that the outlet canal 40 runs, in its second section 73, in the centrifugal direction. It could, for example, also run vertically downwardly directly from the baffle chamber 38 so that, upon reducing the speed of rotation, the fluid is only conveyed by capillary force and not, as previously described, by an additional centrifugal action, into the reception chamber 41.

In one embodiment of the present invention, found in practice to be useful, polymethyl methacrylate is used as the material for the insert element, which has the necessary wetting properties for the fluids usually used in clinical analysis. If the insert elements are to be produced in large numbers as synthetic resin injection molded parts, then polystyrene is an especially preferred material.

In the case of one embodiment of the present invention in which the amount of fluid to be taken up from the mixing valve 26 is 40 to 45 $\mu$l., in practical experiments an outlet canal with a characteristic breadth of from 0.2 to 1 mm. and preferably of 0.5 mm., has proved to be useful, the longitudinal dimension of the cross-section thereby being from about 2 to 4 mm.

Surprisingly, the described mixing valves 26 and 28 according to the present invention permit not only the control of the fluid stream, especially in the case of multi-step analytical processes, but, at the same time, the achievement of a very good mixing up of the fluid. This initially unexpected effect of the construction according to the present invention can probably be explained as resulting from the fact that, in the baffle chamber 38, layers of different concentration form, which are only mixed up relatively slowly. Upon reducing the speed of rotation, these layers then enter into the outlet canal 40 substantially in parallel. They are there mixed during the running out.

After the fluid to be investigated in the insert element 14 has, in the previously described way, run through the mixing valve 26 by reducing and again increasing the speed of rotation, it passes, as described, into the reagent zone 41, which functions as reception chamber. As is to be seen from FIG. 2b, this reagent zone is preferably made deeper than the other reagent zones so that the total volume of fluid can be taken up in this reagent zone.

From there, in the case of again increasing the speed of rotation, it passes through the reagent zones 42 and 43, which are possibly filled with appropriate dry reagents or other devices such as are described in Federal Republic of Germany Patent Specification No. 30 44 385, into the second mixing valve 28. The fluid remains in this mixing valve, as in the first mixing valve 26, so long as the first higher speed of rotation is maintained. When the possibly desired second incubation time has expired, the speed of rotation is reduced, precisely as previously described, and, after filling of the outlet capillary 46, is again increased so that the fluid, due to the manner of working of the mixing valve 28 according to the present invention, passes into the cuvette antechamber 52 and from there into the measuring chamber 50. The second mixing valve is preferably also provided when, as far as the course of the reaction is concerned, a second incubation period is not needed because in this case, too, the device according to the present invention brings about an especially intensive and rapid homogenization of the fluid passed into the baffle chamber 44.

It will be appreciated that the instant specification and examples are set forth by way of illustration and not limitation, and that various modifications and changes may be made without departing from the spirit and scope of the present invention.

What is claimed is:

1. In a device rotatable about an axis of rotation and having a fluid flow canal extending substantially radially outward from an end nearest the axis of rotation and receptive at the end of a volume of fluid for subjecting the same to centrifugal force during rotation, the improvement of fluid controlling and mixing means, comprising: a baffle chamber in the fluid flow canal having a volume sufficiently greater than the volume of the fluid and centrifugal bottom means for forming a steady state fluid surface therein at a first speed of rotation; and outlet canal means in fluid communication with the baffle chamber at one end and having a boundary surface force on the fluid and a portion disposed radially inward of the steady state fluid surface for forcing the fluid from the baffle chamber in response to the boundary surface force when the device is rotating at no greater than a second speed of rotation which is smaller than the first speed of rotation.

2. The device according to claim 1, wherein the end of the outlet canal means in fluid communication with the baffle chamber opens thereinto at a point radially outward of the steady state fluid surface thereby effecting a wettening thereof at the first speed of rotation.

3. The device according to claim 1 or 2, wherein the fluid flow canal further comprises chamber means for providing a capillary-action at the other end of the outlet canal means.

4. The device according to claim 1, wherein the portion of the outlet canal means radially inward of the steady state fluid surface comprises an apex radially inwards from the steady state fluid surface formed in the baffle chamber during the rotation with the first speed of rotation, a first section extending from the end in fluid communication with the baffle chamber up to the apex with a directional component towards the axis of rotation, and a second section extending away from the apex with a directional component radially from the axis of rotation to another end.

5. The device according to claim 4, wherein the other end of the outlet canal means lies further away from the axis of rotation than the centrifugal bottom means of the baffle chamber.

6. The device according to claim 1, wherein the baffle chamber has the smallest possible wetted surface.

7. The device according to claim 1, wherein the baffle chamber further comprises overflow aperture means for limiting the volume of the fluid to that volume forming the steady state fluid surface at the first speed of rotation.

8. A process for controlling and mixing a current of fluid, comprising the steps of: providing a fluid flow passage extending substantially radially outwardly from an axis of rotation and receptive of a maximum volume of fluid for subjecting same to centrifugal force during rotation, at least one baffle chamber in the flow passage having a volume greater than said maximum volume and configured to form a steady state fluid surface therein at a first speed of rotation which is radially outwardly beyond a predetermined extent thereof with respect to the axis of rotation and is closed outwardly of said predetermined extent to prevent flow of the fluid therefrom when the device is rotating at no less than said first predetermined speed of rotation and an outlet passage in fluid communication with the baffle chamber and having walls wettable by the fluid to be controlled, wherein the outlet passage has a portion thereof disposed radially inwardly of the steady state fluid surface at said first speed of rotation and is receptive of the fluid in the baffle chamber in response to boundary surface force when the device is rotating at no greater than a second speed of rotation which is smaller than said first speed of rotation; rotating the passage about the axis of rotation at at least said first speed of rotation to impart centrifugal acceleration greater than gravitational acceleration for a first predetermined period defining the residence time in the baffle chamber; and reducing the speed of rotation to the second speed of rotation for a predetermined second period until the outlet passage is filled.

9. The process according to claim 8, wherein, after filling of the outlet passage, the speed of rotation is again increased to such an extent that the fluid is forced by the centrifugal force out of the outlet passage.

10. A device for the control and mixing of a fluid centrifugally flowed through the device when the device is rotated, comprising:
 a baffle chamber for receiving the fluid and having a fluid inlet opening on one side and a centrifugal bottom on another side; and
 a fluid outlet canal having an opening for receiving the fluid from the baffle chamber, at least a portion which is spaced from the centrifugal bottom toward the baffle chamber, and means comprising walls wettable by the fluid and at least one cross-sectional dimension which is sufficiently smaller than any cross-sectional dimension of the baffle chamber for producing sufficient boundary surface force on the fluid to force the fluid from the baffle chamber, whereby, when the fluid enters the baffle chamber through the inlet opening and the device is rotated about an axis of rotation generally parallel to and spaced from the centrifugal bottom toward the baffle chamber at a sufficient, first speed of rotation, fluid is centrifugally held on the centrifugal bottom and cannot pass the portion of the outlet canal which is spaced toward the baffle chamber therefrom, and when the device is rotated about the axis at a sufficiently-lower, second speed of rotation, the boundary surface forces the fluid from the baffle chamber.

11. The device of claim 10, wherein the opening of the fluid outlet canal from the baffle chamber is close enough to the centrifugal bottom to be wet by the fluid centrifugally held thereby.

12. The device of claim 10, wherein the opening of the fluid outlet canal from the baffle chamber is at the centrifugal bottom, whereby to be wet by the fluid held thereby.

13. The device of claim 10, wherein the fluid outlet canal has an end spaced from the centrifugal bottom away from the baffle chamber, whereby, when the boundary surface force of the fluid outlet canal has forced the fluid to the end, the cohesion of the fluid draws it out of the fluid outlet canal under centrifugal force.

14. The device of claim 10, and further comprising an overflow canal from the baffle chamber spaced from the centrifugal bottom toward the baffle chamber, whereby to limit the volume of the fluid held by the centrifugal bottom to that volume of the baffle chamber between the overflow canal and the centrifugal bottom.

15. A device for the control and mixing of a fluid centrifugally flowed through the device when the device is rotated, comprising:
a baffle chamber having a fluid inlet opening on one side and a centrifugal bottom on the opposite side; and
a fluid outlet canal having an opening at one end of the centrifugal bottom, at least a portion which is spaced from the centrifugal bottom toward the baffle chamber, walls wettable by the fluid, and at least one cross-sectional dimension which is smaller than any cross-sectional dimension of the baffle chamber.

16. The device of claim 15, wherein the fluid outlet canal comprises a first section defined by a baffle wall (74) projecting toward the baffle chamber (38) from the centrifugal bottom (64) to an apex (76) which defines the portion of the fluid outlet canal which is spaced from the centrifugal bottom toward the baffle chamber, and a pair of facing surfaces (65, 67) extending along a side of the baffle chamber between the sides of the fluid inlet opening and the centrifugal bottom and stradling the baffle wall (74).

17. In an element for rotation on the rotor of a centrifugal analyzer having a sample chamber at one end for receiving a fluid sample, a flow canal extending generally radially from the sample chamber when the element is on the rotor to a windowed cuvette, and at least one reagent chamber in the flow canal for adding a reagent to the sample when rotation of the element on the rotor centrifugally flows the fluid sample along the canal to the cuvette, a device for the control and mixing of the fluid sample centrifugally flowed through the device when the device is rotated, comprising:
a baffle chamber further along the flow canal than the reagent chamber and having a fluid inlet opening from the flow canal on the side closest to the reagent chamber, and a centrifugal bottom on the opposite side; and
a fluid outlet canal having an opening at one end of the centrifugal bottom, at least a portion which is spaced from the centrifugal bottom toward the baffle chamber, walls wettable by the fluid, and at least one cross-sectional dimension which is smaller than any cross-sectional dimension of the baffle chamber.

* * * * *